Figure 1:
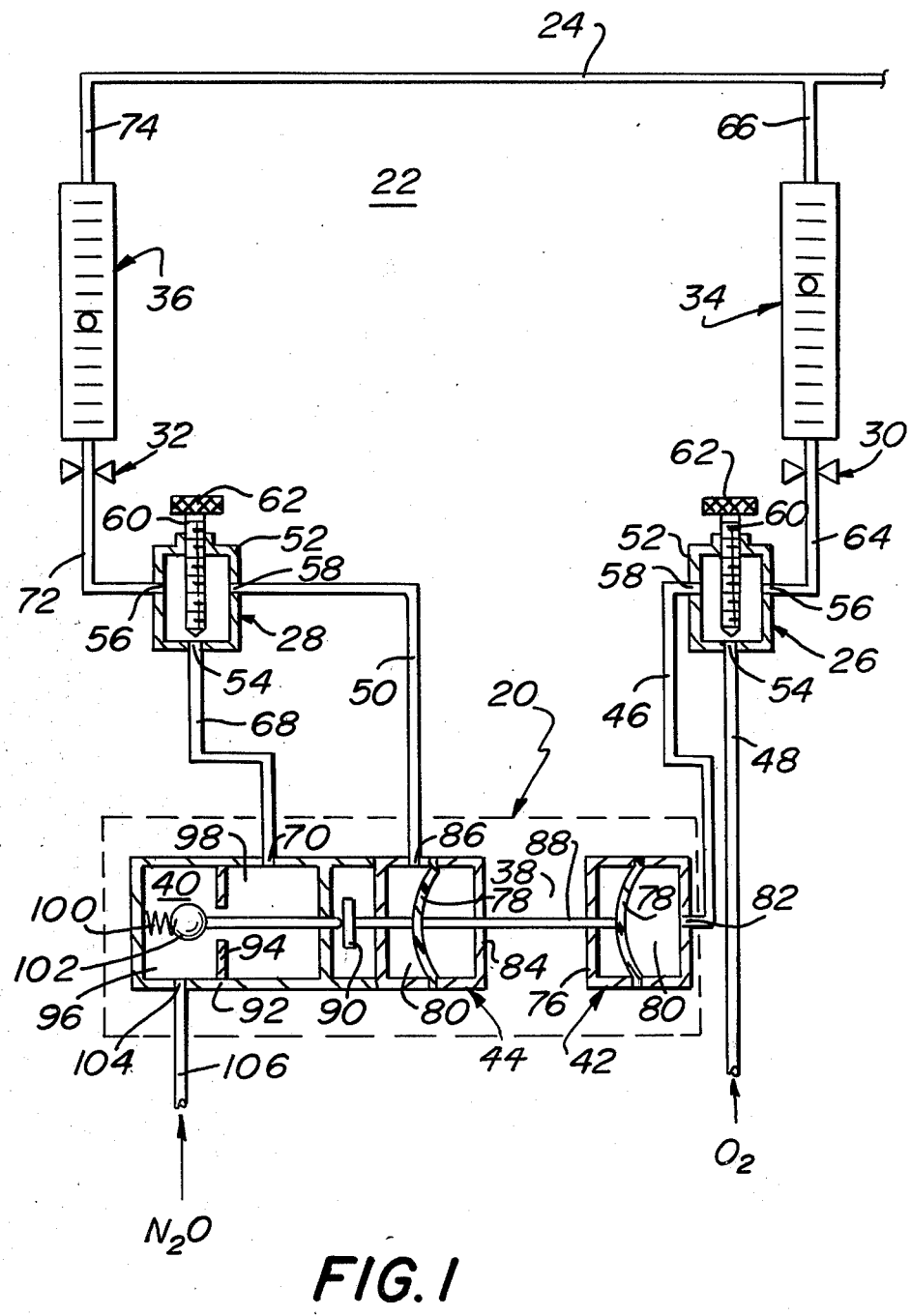

United States Patent [19]

Schreiber

[11] 4,328,823
[45] May 11, 1982

[54] OXYGEN FLOW RATIO CONTROLLER FOR ANESTHESIA APPARATUS

[75] Inventor: Peter J. Schreiber, Zionsville, Pa.

[73] Assignee: N.A.D. Inc., Telford, Pa.

[21] Appl. No.: 149,874

[22] Filed: May 14, 1980

[51] Int. Cl.³ .......................................... G05D 11/03
[52] U.S. Cl. ................................ 137/88; 128/203.14; 128/203.25
[58] Field of Search .......................... 137/88, DIG. 7; 128/203.12, 203.14, 203.25, 205.11

[56] References Cited

U.S. PATENT DOCUMENTS

| | | |
|---|---|---|
| 2,800,915 | 7/1957 | Tavener .............................. 137/88 |
| 3,739,799 | 6/1973 | Bickford et al. ...................... 137/88 |
| 4,015,617 | 4/1977 | Connolly .............................. 137/88 |
| 4,191,952 | 3/1980 | Schreiber et al. ................... 340/611 |

Primary Examiner—William R. Cline
Attorney, Agent, or Firm—Caesar, Rivise, Bernstein & Cohen, Ltd.

[57] ABSTRACT

In anesthesia apparatus for supplying oxygen and an anesthesia gas through respective flow control valves to a patient breathing circuit an oxygen flow ratio controller is provided. The system includes a restrictor in the pipeline of the oxygen flow control valve and a restrictor in the pipeline of the anesthesia gas flow control valve. The oxygen flow ratio controller includes differential pressure sensing means and anesthesia gas flow control means, the differential pressure sensing means includes a diaphragm assembly responsive to the pressure in the oxygen pipeline and another diaphragm assembly responsive to the pressure in the anesthesia gas pipeline and is coupled to the restrictor pipelines. The anesthesia gas flow control means controls the flow of gas to the anesthesia gas pipeline. The diaphragm assemblies are opposed to each other and are coupled together by a displaceable linkage. The linkage is also coupled to the anesthesia gas flow control means to control the flow of anesthesia gas therethrough in response to the differential pressure existing in said pipelines.

6 Claims, 2 Drawing Figures

OXYGEN FLOW RATIO CONTROLLER FOR ANESTHESIA APPARATUS

This invention relates generally to anesthesia apparatus and more particularly to anesthesia gas controllers for anesthesia apparatus.

Anesthesia apparatus commercially available commonly include respective flow control valves for controlling the flow or supply of oxygen and anesthesia gas(es), e.g., nitrous oxide, into a common manifold and from there to a patient breathing circuit. Most apparatus also include sensing means and indicating meters, e.g., flow or rotometers, to indicate the gas flow delivered through the flow control valves as well as other system conditions, e.g., gas pressure.

It is the responsibility of the operator of the anesthesia machine to guarantee that a minimum supply of oxygen is provided in the delivered gas flow. Notwithstanding this responsibility, various accidents have occurred over the past few years when the oxygen percentage decreased below a minimum safety level. Many such accidents have been a result of a failure in the oxygen supply, and inadvertent closing of the oxygen control valve or a misjudgment in the setting of the flows.

Various safety devices are known and commercially available and which respond to the pressure in the oxygen supply line. Such devices signal a decrease or total failure of the oxygen supply pressure. Such devices may also interrupt, or decrease, all gas flows other than oxygen in the event of a partial or total failure of oxygen supply pressure. However, prior art devices which function responsive to oxygen pressure have the major disadvantage that if the oxygen control valve is closed, such that no oxygen is delivered to the patient, the oxygen pressure will still exist in the supply line and the alarm device will not provide an alarm indication even though no oxygen is flowing.

In my U.S. Pat. No. 4,191,952, assigned to the same assignee as this application and whose disclosure is incorporated by reference herein, there is disclosed and claimed a low oxygen flow alarm system for anesthesia apparatus supplying oxygen through one pipeline into a manifold while supplying an anesthesia gas through a second pipeline into the manifold. The alarm system of that invention comprises first pressure actuated means responsive to the oxygen pressure, in the first pipeline and having a first output member whose position is dependent upon the oxygen pressure, second pressure actuated means responsive to the anesthesia gas pressure in the second pipeline and having a second output member whose position is dependent upon the anesthesia gas pressure, and alarm means. The alarm means includes displaceable means. The first and second output members are coupled to the displaceable means and act in opposition thereon so that the first output means tends to move the displaceable means in a first direction while said second output means tends to move the displaceable means in a second and opposite direction. The alarm means includes a switch which produces an alarm signal whenever the displaceable means has been moved in said second direction to a predetermined position.

In U.S. Pat. No. 4,015,617, (Connolly) there is disclosed anesthesia apparatus providing a mixture of oxygen and nitrous oxide gas into a breathing circuit for the patient. The apparatus includes a flow control valve for adjusting the flow of oxygen into the breathing circuit and a nitrous oxide pressure regulator for regulating the nitrous oxide flow in response to monitored oxygen pressure. By varying the oxygen flow control valve, the flow of nitrous oxide is automatically varied to maintain a predetermined gas flow ratio.

While the device disclosed in the Connolly patent appears suitable for its intended purpose, it nevertheless suffers from at least one major drawback, namely, limited utility. In this regard, the Connolly system does not allow independent adjustment of nitrous oxide and oxygen flow. Thus, if one reduces the oxygen flow in the apparatus of the Connolly patent, the system will automatically make a corresponding reduction in the nitrous oxide flow.

The need thus exists for a gas ratio control system for anesthesia apparatus which automatically regulates the ratio of anesthesia gas to oxygen provided into the patient breathing circuit, yet enables independent control of oxygen and anesthesia gas so long as a threshold level of oxygen flow exists.

Accordingly, it is a general object of the instant invention to provide an oxygen flow ratio control system for anesthesia apparatus which overcome the disadvantage of the prior art.

It is a further object of the instant invention to provide an oxygen flow ratio control system which enables the independent adjustment of oxygen and anesthesia gas so long as the flow of oxygen is above a predetermined threshold value.

It is still a further object of the instant invention to provide an oxygen flow ratio control system which is relatively simple in construction.

These and other objects of the instant invention are achieved by providing a gas control system for use with anesthesia apparatus supplying oxygen through one line into a manifold while supplying an anesthesia gas through a second line into the manifold. The first line includes first adjustable means for enabling the adjustment of the flow of oxygen through the first line. The second line includes second adjustable means for enabling the adjustment of the flow of anesthesia gas through the second line. The first and second adjustable means are adjustable independently of each other. The system comprises flow control means coupled to the second line for controlling the flow of gas therethrough, first pressure actuated monitoring means responsive to oxygen pressure in said first line for providing a first signal representative of oxygen pressure, second pressure actuated monitoring means responsive to anesthesia gas pressure in the second line for providing a second signal representative of the anesthesia gas pressure, and means responsive to said first and second pressure actuated means for operating said flow control means in response to the differential pressure monitored by said first and second pressure actuated monitoring means.

Figure 2:
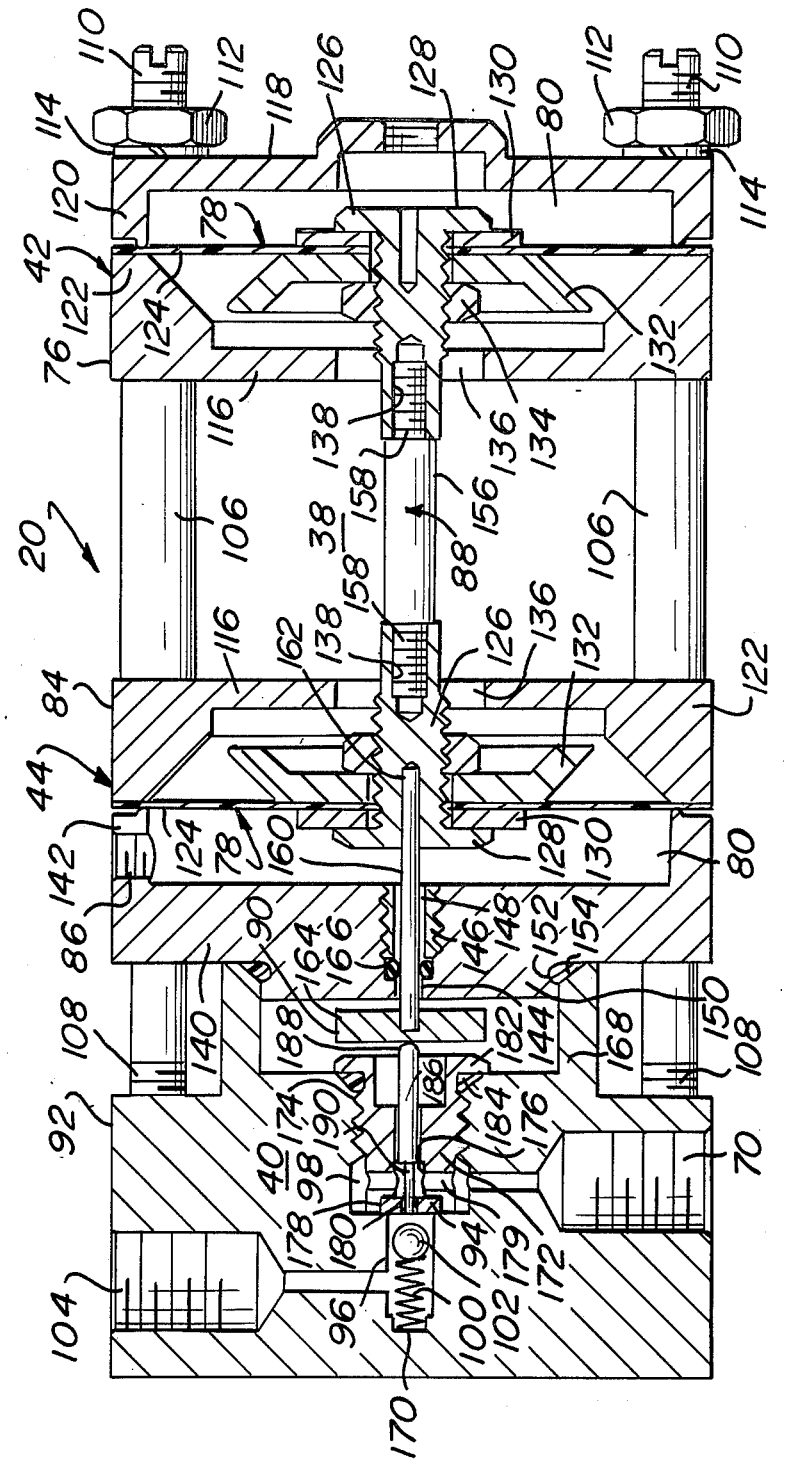

Other objects and many of the attendant advantages of this invention will be readily appreciated as the same becomes better understood by reference to the following detailed description when considered in connection with the accompanying drawing wherein:

FIG. 1 is a schematic diagram of a portion of an anesthesia apparatus including the oxygen flow ratio control system of the instant invention; and FIG. 2 is a sectional view of a portion of the oxygen flow ratio control system of the instant invention.

Referring now to the drawings wherein like reference characters refer to like parts, there is shown generally at 20 in FIG. 1 an oxygen flow ratio control system in an anesthesia apparatus 22 (of which only a relevant portion is shown and described herein). The anesthesia apparatus 22 is of conventional construction and is arranged to provide a mixture of oxygen and anesthesia gas(es) through a manifold 24 for inhalation by the patient. To that end, the apparatus 22 basically comprises a compressed oxygen cylinder (not shown) and compressed anesthesia gas cylinder (not shown). Oxygen and anesthesia gas, e.g., nitrous oxide, are provided via respective flow control valves 26 and 28, respective restrictors 30 and 32, respective flow meters 34 and 36 into the common manifold 24 where the gases mix for supply to the patient breathing circuit (not shown). The flow control valves are manually adjustable to establish the rate of flow of gas therethrough. Each restrictor is a reduced orifice, linear restrictor. The flow meters indicate the rate of gas flow into the manifold.

The oxygen flow ratio control system 20 of the instant invention basically comprises differential pressure sensing means 38 and flow control means 40.

The differential pressure sensing means 38 will be described in detail later, suffice for now to state that it is arranged to monitor the percentage of oxygen in the manifold 24. This is accomplished by comparing the oxygen pressure resulting from the flow of oxygen through resistor 30 to the nitrous oxide pressure resulting from the flow of nitrous oxide through resistor 32. The flow control means 40 is in the form of a valve arranged to adjust the flow of nitrous oxide into the flow control valve 28 under the control of the differential pressure sensing means 38.

The differential pressure sensing means 38 includes a first pressure actuated monitoring unit 42 and a second pressure actuated monitoring unit 44. The monitoring unit 42 includes a diaphragm assembly (to be described in detail later) which is pressurized, via a pilot pipeline 46 from the oxygen flow control valve 26 upstream of the resistor 30. The monitoring unit 44 also includes a diaphragm assembly (to be described in detail later) which is pressurized, via a pilot pipeline 50 from the nitrous oxide flow control valve 28 upstream of the resistor 32.

The flow valves 26 and 28 are each of conventional construction and each includes a housing 52 having a gas inletport 54, a gas outlet port 56, a pilot line port 58 and an adjustable needle valve element 60. A knob 62 is connected to the element 60 of valve 26 for adjusting the rate of oxygen flow through the valve. A similar knob is connected to the needle element of valve 28 for adjusting the nitrous oxide flow therethrough. A pipeline 48 is connected to port 54 of valve 26 to carry oxygen from a tank (not shown) to the valve for distribution to its outlet port 56. The pilot pipeline 46 is connected between the pilot port 58 and the oxygen pressure monitoring unit 42 of the differential pressure sensing means 38. An outlet pipeline 64 is connected between the outlet port 56 and the restrictor 30.

Each of flow meters 34 and 36 is of conventional construction and comprises a tapered glass tube having a gradually increasing inside diameter in the upward direction. The glass tube contains a free-moving float which serves as an indicator of the rate of gas flow through the tube. The tube is graduated in terms of volume per unit time.

As can be seen in FIG. 1 the upper end of flow meter 34 tube is connected to a branch pipeline 66 which forms the oxygen input to the common manifold 24. The inlet port 54 of flow control valve 28 is connected to a pipeline 68 which is in turn connected to the outlet port 70 of flow control means 40 providing the nitrous oxide from its storage tank (not shown). The pilot pipeline 50 is connected between the pilot port 58 of the valve 28 and the nitrous oxide pressure actuated monitoring means 44 of the differential pressure sensing means 38. An outlet pipeline 72 is connected between the outlet port 56 of valve 28 and the restrictor 32. The flow meter 36 is connected between the restrictor 32 and a branch pipeline 74 which serves as a second input to the common manifold 24.

The system 20 is arranged to control or regulate the percentage of oxygen in the oxygen-nitrous oxide mixture. The oxygen concentration is monitored by comparing the ratio of the oxygen flow to the nitrous oxide flow provided into the fresh gas manifold 24. This is accomplished by comparing the oxygen pressure and the nitrous oxide pressure that result from the flow of such gases through restrictors 30 and 32, respectively. As will be appreciated by those skilled in the art, the resulting pressures within the housings of valves 26 and 28 are each a function of the resistance of the associated restrictor and the gas flow through the restrictor. In general, this relationship is not linear, but an increase in flow always produces an increase in pressure. Consequently, the ratio of oxygen pressure to the nitrous oxide pressure is related to the oxygen concentration in the manifold 24.

The pressure ratio is monitored by the differential pressure sensing means 38. As mentioned heretofore the sensing means 38 is in the form of two pressure sensing units 42 and 44. Each unit is separately housed and isolated from each other to insure that the oxygen and the nitrous oxide gases are kept separate. To that end the pressure sensing unit 42 basically comprises an enclosure 76 having a diaphragm assembly 78 disposed therein to form a pressure chamber 80. The enclosure 76 includes a pilot port 82 to which the pilot pipeline 46 is connected and which is in communication with chamber 80. The unit 44 is similar in construction to unit 42 and also has a diaphragm assembly 78 disposed within its enclosure 84 to form a pressure chamber 80. The enclosure 84 includes a pilot port 86 connected to pilot pipeline 50 and in commmunication with chamber 80 of unit 44.

The diaphragm assemblies 78 of units 42 and 44, are connected together by mechanical linkage means 88. The linkage means includes a plunger assembly 90, to be described in detail later, which serves as the output of the differential pressure monitoring means 38 and is coupled to the flow control valve 40. The plunger assembly is arranged to be moved longitudinally, i.e., from right to left (and vice versa) in response to the existing differential pressure as monitored by the differential pressure sensing means 38 so that its longitudinal position is indicative of the existing differential pressure and concomittant gas flow rates. The longitudinal position of the plunger assembly establishes the size of the opening of valve 40 from fully open through partially open to full closed, thereby establishing the rate that anesthesia gas is enabled to flow through the valve.

The flow control valve 40 basically comprises a sealed enclosure 92 having a valve seat 94 dividing the enclosure into an input chamber 96 and an output chamber 98. A bias spring 100 and a moveable ball 102 are disposed in input chamber 96. The plunger assembly 90 is arranged to control the position of the ball 102 with respect to the seat 94 against the bias force provided by spring 100. The enclosure 92 also includes an input port 104 communicating with the input chamber 96. The output port 70 (mentioned earlier) communicates with the output chamber 98. A pipeline 106 is connected to the port 104 to carry nitrous oxide from the tank (not shown) to the valve 40 for distribution to its outlet port 70.

As mentioned heretofore, the linkage means connects the diaphragm assemblies of units 42 and 44 together. The units are in opposition to each other so that the movement of the diaphragm assembly 78 of unit 42 in response to the oxygen pressure opposes the movement of the diaphragm assembly 78 of unit 44 in response to the nitrous oxide pressure. Since the pressure of the oxygen in pilot pipeline 46 and the pressure of the nitrous oxide in pilot pipeline 50 depend not only on the oxygen and nitrous oxide gas flows, respectively, through the respective control valves 26 and 28, but also on the conductance values of the corresponding restrictors 30 and 32, respectively, the conductance of the restrictors are selected so that the linkage assembly 88 moves a first position shown in FIG. 1, when the ratio of the oxygen flow to the nitrous oxide flow (and consequently the oxygen concentration in the fresh gas provided into the manifold) exceeds a predetermined threshold level, e.g., 25 percent. The linkage assembly 88 moves in the opposite direction, i.e., toward a second or closed position if the ratio of the oxygen flow falls below this predetermined value. When the linkage means is in the first position, the plunger assembly 90 raises the ball 102 completely off the valve seat 94 so that the valve 40 is fully open. When the linkage means is in the second position, the bias force provided on the ball 102 by spring 100 causes the ball to seat fully, thereby closing the valve 40. When the linkage means is in any intermediate position between the first and second positions, the valve is partially open, with the size of the opening being dependent on the position of the linkage means.

Operation of the linkage assembly 88 to adjust the control valve 40 is as follows: in the event that the ratio of the oxygen flow to the nitrous oxide flow is above the predetermined threshold level, e.g., 25 percent, the force created by the pressure on the diaphragm of the pressure sensor 42 exceeds the force created by the pressure on the diaphragm of pressure sensor 44 so that the linkage assembly 88 moves to the left to the first position shown in FIG. 1, whereupon the plunger 90 raises the ball in valve 40 fully off its seat 94 against the bias of a spring 100, thereby permitting nitrous oxide to flow from valve output port 104 to the control valve 28. During this condition, the valve 40 is fully open and permits unrestricted control of nitrous oxide flow within the safety limits established by restrictors 30 and 32. As long as the valve 40 is fully open, either the oxygen or the anesthesia gas flow can be independently adjusted by the flow control valves 26 and 28, respectively.

In the event that the flow control valves 26 and 28 are adjusted so that the flow of nitrous oxide would attempt to exceed the safety limit or the flow of oxygen would attempt to drop below the safety limit, the force created by the pressure on the diaphragm assembly 78 of unit 44 exceeds the force created by the pressure on the diaphragm assembly 78 of unit 42, whereupon the plunger assembly 90 moves towards the right to an intermediate position so that the ball moves closer to its seat and the valve 80 is partially open. In such a case, the differential pressure sensing means 38 and the control valve 40 act as a slave pressure regulator, with the opposing forces produced by the diaphragm assemblies adjusting the size of the valve's opening so that the ratio of the oxygen flow to nitrous oxide flow is maintained at the threshold level irrespective of the rate of the flow of oxygen or nitrous oxide established by the setting of the valves 26 and 28, respectively.

In the event that the flow of oxygen is interrupted, such as could occur if the oxygen control valve 26 is accidently closed, the force produced by the diaphragm of unit 44 and the spring 100 exceeds the force produced by the diaphragm of unit 42 and the linkage means moves to the second position wherein the ball 102 is fully seated and the valve 40 is closed.

Referring now to FIG. 2, the details of the differential pressure controller 38 and the flow control valve 40 will be described. As can be seen therein, the unit 42 of the differential controller comprises a housing 76 while the unit 44 comprises a housing 84. The control valve 40 includes a housing 92. The housings 76, 84 and 92 are secured together via plural longitudinally extending rods 106. The free end of each rod is threaded at 108. Each rod extends through aligned openings in the housings 42 and 44 with the threaded end 108 thereof engaged within a threaded opening (not shown) in the housing 92 of valve 40. The opposite end 110 of each rod is in the form of a slotted screw having a hex head nut 112 and a lock washer 114 disposed thereon to secure the housings together.

The housing 76 comprises two hollow flanged sections 116 and 118. Section 118 includes a peripheral flange 120 and section 116 includes a peripheral flange 122. The diaphragm assembly 78 within unit 42 comprises a diaphragm 124 formed of a resilient material and whose periphery is interposed and tightly held between the flanges 120 and 122 of the housing 76. The diaphragm 124 and the interior surface of the section 118 form the input chamber 80 of the unit 42. The diaphragm 124 includes a central opening through which a tubular connector 126 extends. The connector includes an enlarged head in the form of a hex nut 128. A washer 130 is interposed between the head 128 and the periphery of the central opening in the diaphragm 124. A disk 132 having an angularly extending periphery is mounted via a central opening on the body of the connector 126 on the opposite side of the diaphragm from washer 130. The outer periphery of the connector 126 is threaded partially along its body portion and a hex nut 134 is mounted on that portion. The tightening of the hex nut tightly interposes the diaphragm portion contiguous with the central opening tightly between the disk 132 and the washer 130 to effectively seal the chamber 80. The free end of the body of the connector 126 is of reduced diameter and extends out of the housing section 116 through a central opening 136. The reduced diameter portion of the connector 126 includes a longitudinally extending threaded bore 138 which serves as a means for connecting the diaphragm assemblies together, via the linkage means 88 (as will be described later).

The housing 84 of unit 44 is of similar construction to the housing 76 of unit 42 except for one portion thereof. To that end, all of the components of housing 84 which are identical to the components forming unit 42 are given the same reference numerals herein and the description thereof need not be reiterated.

The housing 84 comprises the heretofore mentioned section 116 and a section 140. The section 140 includes a flange 142 which is similar to flange 120 of unit 42. Accordingly, the diaphragm assembly 78 of unit 44 is tightly held between the opposed flanges 142 and 122. The input chamber 80 of unit 44 is formed between the inner surface of the section 140 and the diaphragm 124. The input port 86 extends through the flange portion 142 and into communication with the chamber 80. The section 140 includes a central opening 144 in which is threadedly engaged a nipple or sleeve 146. The nipple includes a smooth central opening 148 through which a portion of plunger assembly 90 extends. The section 140 includes a central projection 150 including a annular recess 152 about its periphery. An O-ring 154 is located in the recess to form a seal with the cooperating portion of the valve 40, housing to be described in detail later.

As mentioned earlier, the linkage assembly 88 connects the oxygen pressure sensing unit 42 to the nitrous oxide pressure sensing unit 44. To that end, linkage means 88 comprises an elongated shaft 156 having a pair of threaded ends 158. One threaded end 158 is threadedly engaged within the bore 138 of the connector forming a portion of the diaphragm assembly of unit 44 while the opposite threaded end of shaft 156 is threadedly engaged in the connector of the diaphragm assembly of unit 42. Thus, the diaphragm assemblies are secured to each other and cannot move independently of each other.

The plunger assembly 90 basically comprises an elongated rod 160 having one end disposed and held within a longitudinally extending bore 162 in the connector 126 of the unit 44. The opposite end of the plunger rod 160 extends through the sleeve 146 out of the housing section 140 and into a central bore in a plunger disk 164. An O-ring 166 is disposed within a annular recess in a portion of the wall of section 140 adjacent the exiting end of plunger pin 160 to seal the interior of chamber 80.

The valve 40 comprises a housing block 92 whose inner face includes a peripheral upstanding wall 168 arranged to receive the projecting portion 150 of unit 44 within its interior and with the O-ring interposed slightly between the wall portion 168 and the portion of section 140 contiguous therewith to seal the interior space in which the plunger disk is located from the ambient atmosphere.

The chamber 96 of valve 40 is in the form of a tubular bore. The helical spring 100 and the ball 102 are located within the bore. The diameter of the bore 96 is slightly greater than the diameter of the ball 102 to enable the ball to roll longitudinally therein. The spring 100 is interposed between the ball and the back wall 170 of the chamber 96. The valve seat 94 is mounted in abutment with the front edge of the chamber 96 and is held in place via a threaded insert or plug 172. The plug 172 is a threaded member threadedly engaged within a bore 174 in the housing wall 92 opening to the mouth of the chamber 96. The plug 172 includes a central passageway 176 extending therethrough and terminating at one end in a annular recess 178 in which the valve seat 94 is located. The plug 172 is of reduced diameter adjacent the valve seat to form the output chamber 98. A plurality of radially extending openings 179 provide communication between the annular chamber 98 and the central opening 176 in the plug 172. The valve seat 94 includes a central opening 180 which communicates with the chamber 98. The outlet port 70 of valve 40 extends into the body of housing portion 92, and communicates with the chamber 98. The plug 172 includes a flanged cap 182. An O-ring 184 is interposed between the flanged cap and the contiguous surface of the housing wall 92 to form a seal. The inlet port 104 of the valve 40 communicates with the chamber 96.

The plunger assembly 90 also includes a second plunger pin 186 located within passageway 176 in plug 172. The pin 186 is an elongated member having a rounded end 188 adapted to engage the plunger disk 164 and a reduced diameter end 190 adapted to engage the ball 102 of the valve 40. The plunger pin 186 is adapted to be reciprocated through the passageway by the plunger disk 164.

Operation of the differential pressure sensor 38 and the valve 40 is as follows: When the ratio of the pressure monitored from the pilot pipeline 46 and the nitrous oxide pilot pipeline 50 is in excess of the desired threshold level, e.g., 25 percent oxygen, the pressure in chamber 80 of unit 42 exceeds the pressure in chamber 80 of unit 44, whereupon diaphragm 124 in unit 42 moves outward while the diaphragm in unit 44 moves inward. Since the two diaphragm assemblies are connected together by shaft 156 of the linkage means, the linkage means 88 moves to the left to the position shown in FIG. 1. The leftward movement of the linkage means causes the pin 160 to move to the left, thereby carrying the plunger disk 164 to the left and into engagement with the rounded end 188 of the plunger pin 186. This action moves the plunger pin 186 to the left so that its reduced diameter end 190 contacts the ball 102 to lift the ball from its seat against the bias provided by spring 100. Accordingly, the nitrous oxide is enabled to flow from the input port 104 of valve 40 through the chamber 96, the communicating opening 180 in the valve seat and the annular chamber 98 to the outlet port 70 and hence to the nitrous oxide flow valve 28.

In the event that either valve 26 or 28 is adjusted so that the ratio of oxygen flow to nitrous oxide flow would be less than the threshold value, the pressure existing in the chambers 80 of units 42 and 44 is such that the linkage assembly moves to the right so that the ball 102 is positioned closer to its seat, and the valve is partially open. This action has the effect of regulating the flow of nitrous oxide through the valve 40 so that the ratio of oxygen-to-nitrous oxide flowing into the manifold is maintained at the desired threshold level.

In the event that the flow of oxygen is interrupted, the differential pressure controller moves the ball onto the valve seat 94, whereupon the flow of nitrous oxide to valve 28 is stopped. In such an event, an alarm signal is provided by means (not shown and not forming any portion of this invention) to operating personnel warning them of the danger condition.

It must be pointed out at this juncture that while the device disclosed herein makes use of mechanical means for controlling the flow of nitrous oxide in response to monitored flows of oxygen and nitrous oxide, it is clear that electrical, e.g., solid state, means can be utilized to provide signals indicative of the differential pressure and for opening and closing a nitrous oxide control valve in response to the differential pressure so monitored.

Moreover, the system of the instant invention can with slight modification be used in systems providing more than one anesthesia gas.

As should be apparent from all of the foregoing the oxygen flow ratio controller of the instant invention is relatively simple in construction, yet offers wide utility since it effects automatic control and regulation of the ratio of oxygen to anesthesia gas provided into the patient breathing circuit, without sacrificing independent control and adjustment of either oxygen or anesthesia gas.

Without further elaboration, the foregoing will so fully illustrate my invention that others may, by applying current or future knowledge, readily adapt the same for use under various conditions of service.

What is claimed as the invention is as follows:

1. A gas control system for use with anesthesia apparatus supplying oxygen through one line into a manifold while supplying an anesthesia gas through a second line into the manifold, said first line including first adjustable means for enabling the adjustment of the flow of oxygen through said first line, said second line including second adjustable means for enabling the adjustment of the flow of anesthesia gas through said second line, said first and second adjustable means being adjustable independently of each other, said system comprising flow control means coupled to said second line and capable of being fully open, partially open, or closed for controlling the flow of gas through said second line, first pressure actuated monitoring means responsive to oxygen pressure in said first line for providing a first pressure signal representative of oxygen flow, second pressure actuated monitoring means responsive to anesthesia gas pressure in said second line for providing a second pressure signal representative of said anesthesia gas flow, and means responsive to said pressure signals from first and second pressure actuated monitoring means for operating said flow control means in response to the differential pressure monitored by said first and second pressure actuated monitoring means, whereupon whenever the flow of oxygen drops below a first predetermined minimum level said flow control means closes to stop the flow of anesthesia gas into said manifold, whenever the ratio of the flow of oxygen to the flow of anesthesia gas is above a second predetermined level and the flow of oxygen is above said first predetermined minimum level said flow control means opens fully to permit said gases to flow into said manifold in the ratio as established by said first and second adjustable means, and whenever the ratio of the flow of oxygen to the flow of anesthesia gas reaches said second predetermined level and the flow of oxygen is above said first predetermined level said flow control means opens partially to a position to adjust the flow of anesthesia gas to maintain said second predetermined level.

2. The gas control system of claim 1 wherein said first pressure actuated monitoring means has a first output member whose position is dependent upon said oxygen flow, the position of said first output member establishing said first signal, second pressure actuated monitoring means having a second output member whose position is dependent upon anesthesia gas flow, the position of said second output member establishing said second signal, said means responsive to said first and second pressure actuated monitoring means comprising displaceable means coupled to said first and second output members and to said flow control means, said first and second output members acting in opposition to each other on said displaceable means, whereupon said first output member tends to move the displaceable means in a first direction while said second output member tends to move the displaceable means in a second direction, said flow control means controlling the flow of anesthesia gas through said second line in response to the position of said displaceable means.

3. The gas control system of claim 2 wherein said first line includes a first restrictor therein and wherein said second line includes a second restrictor therein, said restrictors establishing the ratio of anesthesia gas to oxygen provided by said lines into the manifold.

4. The gas control system of claim 3 wherein said displaceable means is movable to any position between a first position and a second position, said system being arranged such that when said displaceable means is in said first position anesthesia gas is enabled to flow through said second line at a rate which does not exceed a first predetermined percentage of the rate of oxygen flow into said manifold.

5. The gas control system of claim 4 whereupon when said displaceable means is in an intermediate position between said first position and said second position the anesthesia gas is enabled to flow through said second line at a rate which is equal to said first predetermined percentage of said oxygen flow rate.

6. The gas control system of claim 5 wherein said flow control means comprises a valve, wherein said first pressure actuated monitoring means comprise a first movable diaphragm, said second pressure actuated monitoring means comprises a second moveable diaphragm and said displaceable means comprises linkage means interconnecting said first and second diaphragms and said valve.

* * * * *